(12) United States Patent
Shin et al.

(10) Patent No.: US 10,421,793 B2
(45) Date of Patent: Sep. 24, 2019

(54) PROTON-TRANSPORT VESICLE HAVING RECONSTITUTED HETEROLOGOUS PHOTOSENSITIVE PROTEINS AND METHOD FOR PREPARING SAME

(71) Applicant: INDUSTRY-UNIVERSITY COOPERATION FOUNDATION SOGANG UNIVERSITY, Seoul (KR)

(72) Inventors: Kwan Woo Shin, Seoul (KR); Hee Yeon Kim, Gyeonggi-do (KR); Kwang-Hwan Jung, Gyeonggi-do (KR); Keel Yong Lee, Seoul (KR); Tae Kyu Ahn, Gangnam-gu (KR)

(73) Assignee: INDUSTRY-UNIVERSITY COOPERATION FOUNDATION SOGANG UNIVERSITY, Seoul (KR)

( * ) Notice: Subject to any disclaimer, the term of this patent is extended or adjusted under 35 U.S.C. 154(b) by 259 days.

(21) Appl. No.: 15/517,887

(22) PCT Filed: Oct. 10, 2014

(86) PCT No.: PCT/KR2014/009544
§ 371 (c)(1),
(2) Date: Apr. 7, 2017

(87) PCT Pub. No.: WO2016/056691
PCT Pub. Date: Apr. 14, 2016

(65) Prior Publication Data
US 2017/0320923 A1  Nov. 9, 2017

(51) Int. Cl.
| | | |
|---|---|---|
| *C07K 14/415* | (2006.01) | |
| *A01H 5/00* | (2018.01) | |
| *C12N 15/64* | (2006.01) | |
| *C12N 15/70* | (2006.01) | |
| *G01N 33/52* | (2006.01) | |

(52) U.S. Cl.
CPC ............ *C07K 14/415* (2013.01); *A01H 5/00* (2013.01); *C12N 15/64* (2013.01); *C12N 15/70* (2013.01); *G01N 33/52* (2013.01)

(58) Field of Classification Search
CPC ................. C07K 14/415; C07K 19/00
See application file for complete search history.

(56) References Cited

FOREIGN PATENT DOCUMENTS

| EP | 0 073 628 | 3/1983 | ............... G03C 1/72 |
| KR | 10-2015-0034856 | 4/2015 | ............ C07K 19/00 |
| KR | 10-1590606 | 1/2016 | ............ C07K 19/00 |

OTHER PUBLICATIONS

Ernst, O. et al., Chemical Reviews, 2014; vol. 114, pp. 126-163.*
Inoue, K. et al. , 2015; Trends in Microbiology, vol. 23, No. 2, pp. 91-98.*
Tunuguntla, R. et al. Biophysical Journal, vol. 105 Sep. 2013; pp. 1388-1396. (Year: 2013).*
Claassens, N., et al. (2013) "Potential of proton-pumping rhodopsins: engineering photosystems into microorganisms.", *Trends in Biotechnology*, 31(11):633-642.
Finkel, O., et al. (2013) "Short Communication: Global abundance of microbial rhodopsins." , *The ISME Journal*, 7:448-451.
Gruszecki, W., et al. (1997) "The effect of blue light on electron transport in photosystem II reconstituted in planar bilayer lipid membrane.", *Journal of Photochemistry and Photobiology B: Biology*, 39:265-268.
Tunuguntla, R., et al. (2013) "Lipid bilayer composition can influence the orientation of proteorhodopsin in artificial membranes.", *Biophysical Journal*, 105(6):1388-1396.
International Search Report (ISR) in PCT/KR2014/009544, dated Jul. 15, 2015 published in WO 2016/056691.

* cited by examiner

*Primary Examiner* — Russell Kallis
(74) *Attorney, Agent, or Firm* — Harness, Dickey & Pierce, P.L.C.

(57) ABSTRACT

The present invention relates to a proton-transport vesicle and a method for preparing the same, the proton-transfer vesicle comprising: (a) a single phospholipid bilayer liposome; (b) a rhodopsin protein; and (c) a photosystem II protein, wherein the rhodopsin protein and the photosystem II protein are inserted and located in a bilayer of the liposome. Since the heterologous photosensitive proteins are inserted and located in the bilayer of the liposome, the vesicle has an absorption wavelength band of the whole region of visible light by utilizing absorption bands of different lights of the respective photosensitive proteins. Thus, the restricted efficiency caused by utilizing only a specific wavelength in existing organisms or artificial vesicles was improved, and the wavelength region can be enlarged to the all wavelength ranges of visible light.

9 Claims, 6 Drawing Sheets

Specification includes a Sequence Listing.

SEQUENCE LISTING

```
<160> NUMBER OF SEQ ID NOS: 1

<210> SEQ ID NO 1
<211> LENGTH: 750
<212> TYPE: DNA
<213> ORGANISM: unknown
<220> FEATURE:
<223> OTHER INFORMATION: uncultured marine gamma proteobacterium
      EBAC31A08 BAC sequence

<400> SEQUENCE: 1
atgaaattat tactgatatt aggtagtgtt attgcacttc ctacatttgc tgcaggtggt      60
ggtgaccttg atgctagtga ttacactggt gtttcttttt ggttagttac tgctgcttta     120
ttagcatcta ctgtattttt ctttgttgaa agagatagag tttctgcaaa atggaaaaca     180
tcattaactg tatctggtct tgttactggt attgctttct ggcattacat gtacatgaga     240
ggggtatgga ttgaaactgg tgattcgcca actgtattta gatacattga ttggttacta     300
acagttcctc tattaatatg tgaattctac ttaattcttg ctgctgcaac taatgttgct     360
ggatcattat ttaagaaatt actagttggt tctcttgtta tgcttgtgtt tggttacatg     420
ggtgaagcag gaatcatggc tgcatggcct gcattcatta ttgggtgttt agcttgggta     480
tacatgattt atgaattatg ggctggagaa ggaaaatctg catgtaatac tgcaagtcct     540
gctgtgcaat cagcttacaa cacaatgatg tatattatca tctttggttg ggcgatttat     600
cctgtaggtt atttcacagg ttacctgatg ggtgacggtg gatcagctct taacttaaac     660
cttatctata accttgctga ctttgttaac aagattctat ttggtttaat tatatggaat     720
gttgctgtta aagaatcttc taatgcttaa                                      750
```

PROTON-TRANSPORT VESICLE HAVING RECONSTITUTED HETEROLOGOUS PHOTOSENSITIVE PROTEINS AND METHOD FOR PREPARING SAME

CROSS-REFERENCE TO RELATED APPLICATIONS

This application is a national phase application of PCT Application No. PCT/KR2014/009544, filed on Oct. 10, 2014. The entire disclosures of the applications identified in this paragraph are incorporated herein by reference.

FIELD

The present invention was made with the support of the Ministry of Science, ICT, and Future Planning of the Republic of Korea, under Project No. 201331025, which was conducted under the research project entitled "Mid-Carrier Researcher Support Program Advanced Research" within the project named "Study on Artificial Cell Structure and Function Simulation" by the National Research Foundation of Korea under the management of the National Research Foundation of Korea, from 1 May 2013 to 30 Apr. 2014.

The present invention relates to proton-transport vesicles reconstituted with microbial-derived rhodopsin and plant-derived photosystem II proteins and to a method for preparing the same.

BACKGROUND

Most significant biological phenomena, such as signaling and energy production in living organisms, are caused by the ion concentration difference between the inside and the outside of cells. Representative examples of photosensitive proteins performing these actions are photosystem II and rhodopsin proteins. The photosensitive proteins make an ionic difference between the inside and the outside of the cells through structural changes, and thus, play a key role in energy production and signaling. Therefore, the photosensitive proteins are utilized in the treatment of incurable diseases, solar cells, photo-catalysts, and the like through structural analysis.

However, the structural change of each protein significantly depends on the wavelength of light, and thus, has a limit thereof. Therefore, it is important to realize artificial evolution through the reconstitution of photosystem II and rhodopsin proteins into cells to extend the operation wavelength ranges of the proteins to the entire range of visible light. This fact can induce a remarkable development in high-efficiency solar cells, photo-catalysts, or medical treatment employing wide wavelength ranges, which could not be applied by existing techniques.

The reconstitution of membrane proteins has already been widely used for various purposes in cell membrane studies and membrane protein-related studies since the insertion into liposomes made of artificial phospholipid molecules has first been known by Kagawa and Racker in 1971 (*J. Biol. Chem.* 246, 1971, 5477; *Int. J. Biochem.* 20, 1988, 889).

In addition, conventional inventions and studies merely suggested that a single photosensitive protein is inserted into the cellular membrane to check the state of the protein and reproduce existing phenomena, and thus had a drawback in that only some wavelength ranges of visible light are used.

Moreover, the technology has not yet been presented that maximizes the photosensitivity to light and extends the function of separating ions by reconstituting two or more heterologous proteins into a single phospholipid vesicle.

Accordingly, the present inventors have recognized that, if heterologous proteins can be operated at the same time, the functions of the proteins can be performed at the entire wavelength of visible light, UV light, and even a portion of infrared light.

Throughout the entire specification, many papers and patent documents are referenced and their citations are represented. The disclosures of the cited papers and patent documents are entirely incorporated by reference into the present specification, and the level of the technical field within which the present invention falls and the details of the present invention are thus explained more clearly.

DETAILED DESCRIPTION

Technical Problem

The present inventors have endeavored to develop a proton-transport system having high-efficiency characteristics of ion transport for a wide range of visible light by reconstituting heterologous proteins into a single cellular membrane. The present inventors have verified that, as a result of reconstitution of a microbial-derived rhodopsin protein and a photosystem II, which is a plant-derived photosensitive protein, into a single cellular membrane, the absorption wavelength bands of the entire region of visible light can be used by utilizing different light absorption bands of the rhodopsin protein and the photosystem II protein and the respective proteins can respond to light to separate charges very effectively, and thus, the present inventors have completed the present invention.

Therefore, an aspect of the present invention is to provide proton-transport vesicles.

Another aspect of the present invention is to provide a method for preparing proton-transport vesicles of the present invention.

Other purposes and advantages of the present invention will become more obvious with the following detailed description of the invention, claims, and drawings.

Technical Solution

In accordance with an aspect of the present invention, there are provided proton-transport vesicles, each including: (a) a single phospholipid bilayer liposome; (b) a rhodopsin protein; and (c) a photosystem II protein, wherein the rhodopsin protein and the photosystem II protein are inserted in the bilayer of the liposome.

The present inventors have endeavored to develop a proton-transport system having high-efficiency characteristics of ion transport for a wide range of visible light by reconstituting heterologous proteins into a single cellular membrane. The present inventors have verified that, as a result of reconstitution of a microbial-derived rhodopsin protein and a photosystem II, which is a plant-derived photosensitive protein, into a single cellular membrane, the absorption wavelength bands of the entire region of visible light can be used by utilizing different light absorption bands of the rhodopsin protein and the photosystem II protein and the respective proteins can respond to light to separate charges very effectively.

The proton-transport vesicle of the present invention basically includes: (a) a single phospholipid bilayer liposome; (b) a rhodopsin protein; and (c) a photosystem II protein, wherein the rhodopsin protein and the photosystem II protein are inserted in the bilayer of the liposome.

As used herein, the term "proton-transport vesicle" refers to a vesicle that generates and transports protons (H+) by photosensitive proteins as membrane proteins.

As used herein, the term "liposome" refers to a spherical phospholipid vesicle of colloidal particles that self-associate. The liposome composed of amphipathic molecules each having a water-soluble head (hydrophilic group) and an insoluble tail (hydrophobic group) shows a structure in which the molecules spontaneously bind to each other and are arranged due to the interaction therebetween. Liposomes, depending on their size and lamellarity, are classified into small unilamellar vesicles (SUV), large unilamellar vesicles (LUV), and multilamellar vesicles (MLV), but the liposomes included in the present invention are the small unilamellar vesicles (SUV) or the large unilamellar vesicles (LUV). The liposome showing various types of lamellarity as described above has a double-membrane structure similar to the cellular membrane.

The phospholipids used in the proton-transport vesicle of the present invention, which are used as amphiphilic lipids, include natural phospholipids and synthetic phospholipids, and include preferably phospholipids having a $C_{12}$-$C_{24}$ fatty acid chain. Examples of the phospholipid that can be used in the present invention include phosphatidylcholine (PC; natural or synthetic) or lecithin, dipalmitoyl phosphatidylcholine, phosphatidic acid (PA), lysophosphatidylcholine (LPC), phosphatidylserine (PS), phosphatidylethanolamine (PE), phosphatidylglycerol (PG), phosphatidylinositol (PI), phosphocholine phosphoethanolamine, sphingomyelin, cardiolipin, fatty acids prepared from the hydrolysis thereof (fatty acids having a phosphate group), derivatives thereof, or mixtures thereof, but are not limited thereto.

According to a preferable embodiment of the present invention, the phospholipid used in the present invention is POPC (1-palmitoyl-2-oleoyl-sn-glycero-3-phosphocholine) and POPE (1-palmitoyl-2-oleoyl-sn-glycero-3-phosphoethanolamine).

The organic solvent used in the preparation of the proton-transport vesicles of the present invention is methanol, ethanol, n-propanol, butanol, or chloroform, and preferably chloroform.

As used herein, the term "rhodopsin protein" refers to a biological pigment present in biological photo-receptor cells. The rhodopsin protein is synthesized in the cytoplasm and located in the cell membrane, and functions to perceive light.

According to a preferable embodiment, the rhodopsin protein is a microbial-derived rhodopsin protein.

As used herein, the term "microbial-derived rhodopsin protein" is used interchangeably with the term "proteorhodopsin", wherein the proteorhodopsin (PR) is a transmembrane protein that has a structure of seven lipid membrane-spanning α-helices that form a generally cylinder shaped channel. The proteorhodopsin is a photo-active type I retinal-binding protein, which is identified by metagenomic analysis of marine γ-proteobacteria. After the PR was first identified in the SAR86 group of γ-proteobacteria, a plurality of proteorhodopsin variants were found in γ-proteobacteria and α-proteobacteria in Monterey Bay, Hawaii Ocean Time (HOT), Palmer station (Antarctica), the Mediterranean Sea, the Red Sea, and the Sargasso Sea.

It would be obvious to a person skilled in the art that biological function equivalents that can be included in the microbial-derived rhodopsin protein used in the present invention will be limited to the variation of the amino acid sequence exhibiting biological activity equivalent to the microbial-derived rhodopsin protein.

Such amino acid variation is made on the basis of relative similarity, for example, hydrophobicity, hydrophilicity, charge, size, or the like, of amino acid side chain substituents. It can be seen from the analysis of size, shape, and type of the amino acid side chain substitutions that: all of arginine, lysine, and histidine are positively charged residues; alanine, glycine, and serine have similar sizes; and phenylalanine, tryptophan, and tyrosine have similar shapes. Therefore, on the basis of this consideration, arginine, lysine, and histidine; alanine, glycine, and serine; and phenylalanine, tryptophan, and tyrosine may be considered to be biologically functional equivalents.

For introducing such variations, hydropathic indexes of amino acids may be considered. Each amino acid has been assigned a hydropathic index on the basis of its hydrophobicity and charge characteristics: isoleucine (+4.5); valine (+4.2); leucine (+3.8); phenylalanine (+2.8); cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5)

The hydrophobic amino acid indexes are very important in giving interactive biological functions of proteins. It is well known that amino acids with similar hydrophobic indexes need to be substituted with each other to retain similar biological activities. In cases where a variation is introduced with reference to the hydrophobic indexes, the substitution is made between amino acids having a difference in the hydrophobic index within preferably ±2, more preferably ±1, and still more preferably ±0.5.

Meanwhile, it is also well known that the substitution between amino acids with similar hydrophilicity values results in proteins having equivalent biological activity. As disclosed in U.S. Pat. No. 4,554,101, each amino acid residue has been assigned the following hydrophilicity values: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4)

In cases where a variation is introduced with reference to the hydrophilic indexes, the substitution is made between amino acids having a difference in hydrophilicity value within preferably ±2, more preferably ±1, and still more preferably ±0.5.

The exchange of amino acid residues that does not substantially impair protein activity is well known to one skilled in the art (H. Neurath, R. L. Hill, *The Proteins*, Academic Press, New York, 1979). The most common exchanges are exchanges between amino acid residues Ala/Ser, Val/Ile, Asp/Glu, Thr/Ser, Ala/Gly, Ala/Thr, Ser/Asn, Ala/Val, Ser/Gly, Thr/Phe, Ala/Pro, Lys/Arg, Asp/Asn, Leu/Ile, Leu/Val, Ala/Glu, and Asp/Gly.

Preferably, the nucleotide sequence encoding the microbial-derived rhodopsin protein used in the present invention has SEQ ID NO: 1.

The nucleotide sequence used in the present invention is construed to also include a nucleotide sequence that exhibits substantial identity with respect to the nucleotide sequence, in addition to the foregoing sequence. The substantial identity means that, when the present nucleotide sequence and any difference sequence are aligned to correspond to each other as much as possible and the aligned sequences are analyzed using an algorithm that is ordinarily used in the art, the nucleotide sequences show at least 80% homology, preferably at least 90% homology, and most preferably at least 95% homology. Methods of alignment for sequence comparison are known in the art. Various methods and algorithms for the alignment are disclosed in Smith and Waterman, Adv. Appl. Math. 2:482(1981); Needleman and Wunsch, *J. Mol. Bio.* 48:443(1970); Pearson and Lipman, *Methods in Mol. Biol.* 24: 307-31(1988); Higgins and Sharp, *Gene* 73:237-44(1988); Higgins and Sharp, *CABIOS* 5:151-3(1989); Corpet et al., *Nuc. Acids Res.* 16:10881-90(1988); Huang et al., *Comp. Appl. BioSci.* 8:155-65(1992) and Pearson et al., Meth. Mol. Biol. 24:307-31(1994). The NCBI Basic Local Alignment Search Tool (BLAST) (Altschul et al., *J. Mol. Biol.* 215:403-10(1990)) is available from several sources, including the National Center for Biological Information (NCBI), and on the Internet, for use in connection with the sequence analysis programs blastp, blasm, blastx, tblastn, and tblastx. BLSAT can be accessed through www.ncbi.nlm.nih.gov/BLAST/. The sequence identity comparison method using such a program can be confirmed in www.ncbi.nlm.nih.gov/BLAST/blast_help.html.

As used herein, the term "photosystem II protein" refers to a membrane protein in the chloroplast thylakoid, and to a photosensitive protein.

According to another preferable embodiment of the present invention, the photosystem II protein is a plant-derived protein. The plant is more preferably selected from the group consisting of spinach, *Arabidopsis thaliana*, rice, and corn, and still more preferably spinach or *Arabidopsis thaliana*.

The microbial-derived rhodopsin protein and plant-derived photosystem II protein, as membrane proteins, are proteins that can transport the protons ($H^+$), generated from water degraded by irradiated light, to the inside or outside of the cellular membrane, and perform the most effective function, particularly in the wavelength range of visible light.

Still another preferred embodiment of the present invention, the rhodopsin protein absorbs 500- to 600-nm light, corresponding to green wavelength in the wavelength range of visible light, to generate protons.

Another preferred embodiment of the present invention, the photosystem II protein absorbs 400- to 500-nm light and 600- to 700-nm light, respectively corresponding to blue wavelength and red wavelength in the wavelength range of visible light, to generate protons In cases of the rhodopsin protein used in the present invention, the efficiency thereof is remarkably reduced in the blue and red wavelength ranges (400-500 nm and 600-700 nm) compared with the green wavelength range (500-600 nm), and the absorption spectrum of the rhodopsin is great in the green wavelength region (FIG. 2). On the other hand, plants start a water decomposition process, which is the first step in the photosynthesis function, by scattering sunlight in the green region and absorbing blue and red lights. Contrary to rhodopsin, the photosystem II protein of plants has a higher light absorption rate in the red and blue wavelength regions than in the green wavelength region (FIG. 2).

The proton-transport vesicles of the present invention perform the functions of proteins even in the entire wavelength region of visible light, UV light, and even some wavelength bands of infrared light by inserting heterologous proteins, that is, the microbial-derived rhodopsin protein and the plant-derived photosystem II protein, into the bilayer of the liposome, so that a proton transport system can be achieved that has high-efficiency characteristics of proton transport for a wide wavelength range.

In accordance with another aspect of the present invention, there is provided a method for preparing proton-transport vesicles, the method including the steps of: (a) preparing a photosystem II protein; (b) preparing a a rhodopsin protein; (c) hydrating lipids to prepare vesicles; (d) freezing and thawing the vesicles in step (c); (e) reacting the product in step (d) with a surfactant; and (f) reacting the product in step (e) with the photosystem II protein in step (a) and the rhodopsin protein in step (b).

Since the method of the present invention is a process for preparing the above-described proton-transport vesicle of the present invention, the descriptions of overlapping contents therebetween will be omitted to avoid excessive complexity of the specification due to repetitive descriptions thereof.

The method of the present invention for preparing proton-transport vesicles is described step by step in detail as follows:

(a) Preparing Photosystem II Protein

According to a preferable embodiment of the present invention, the preparation of the photosystem II protein (step (a)) includes the following steps: (i) reacting plant leaves with a buffer A solution containing a milk powder or sorbitol, NaCl, $MgCl_2$, Tricine, KOH, PMSF, benzamidine, and ε-aminocaproic acid; (ii) filtering and centrifuging the product in step (i) and removing the supernatant, followed by reaction with the buffer A solution in step (i); (iii) centrifuging the product in step (ii) and removing the supernatant, followed by reaction with a buffer B solution containing NaCl, $MgCl_2$, Tricine, KOH, PMSF, benzamidine, and ε-aminocaproic acid; (iv) centrifuging the product in step (iii) and removing the supernatant, followed by reaction with a buffer C solution containing NaCl, $MgCl_2$, and Hepes KOH; (v) centrifuging the product in step (iv) and then obtaining a frozen thylakoid membrane using liquefied nitrogen; and (vi) melting the frozen thylakoid membrane in step (v), followed by reaction with a gradient solution containing sucrose, Hepes, and a surfactant, and then isolating a photosystem II protein using the sucrose density.

As for the photosystem II protein used in the present invention, a thylakoid membrane is obtained from various plants known in the art and a photosystem II protein is isolated from the thylakoid membrane using a sucrose gradient method.

(b) Preparing Rhodopsin Protein

According to another preferable embodiment of the present invention, the preparation of the rhodopsin protein (step (b)) includes the following steps: (i) inserting a nucleotide sequence encoding a microbial-derived rhodopsin protein into an expression vector to construct a recombinant vector; (ii) introducing the recombinant vector into a host cell to produce a transformant; and (iii) culturing the transformant to express the microbial-derived rhodopsin protein to obtain a rhodopsin protein.

The method of the present invention for preparing the microbial-derived rhodopsin protein is described step by step in detail as follows:

(i) Constructing Recombinant Vector

First, the method of the present invention includes a step for inserting a nucleotide sequence encoding a microbial-derived rhodopsin protein into an expression vector to construct a recombinant vector.

As for the nucleotide sequence of the microbial-derived rhodopsin protein, nucleotide sequences of various microbial-derived rhodopsin proteins known in the art may be used, and preferably, SEQ ID NO: 1 may be used.

As used herein, the term "expression vector" is a linear or circular DNA molecule comprising a fragment encoding a polypeptide of interest operably linked to an additional fragment provided for the transcription of an expression vector. Such an additional fragment includes a promoter and a stop codon sequence. The expression vector includes at least one replication origin, at least one selection marker, a polyadenylation signal, and the like. The expression vector is generally originated from plasmid or viral DNA or from both.

The vector system of the present invention can be constructed by various methods known in the art, and a specific method thereof is disclosed in Sambrook et al., *Molecular Cloning*, A Laboratory Manual, Cold Spring Harbor Laboratory Press (2001), which is incorporated herein by reference.

The nucleotide sequences encoding enzymes involved in the preparation of the microbial-derived rhodopsin protein of the present invention is operably linked to the expression control sequence and may be inserted into the expression vector. The term "operably linked" indicates that a nucleic acid fragment is combined with another nucleic acid fragment, and thus the functions or expression thereof are effected by another nucleic acid fragment. In addition, the term "expression control sequence" means a DNA sequence that controls the expression of an operably linked nucleic acid sequence in a particular host cell. Such an expression control sequence includes a promoter for initiating transcription, any operator sequence for controlling transcription, a sequence for encoding a suitable mRNA ribosomal binding site, and a sequence for controlling the termination of transcription and translation.

The vector of the present invention may typically be constructed as a vector for expression. In cases where the vector of the present invention is an expression vector and uses a prokaryotic cell as a host cell, the vector includes a strong promoter to initiate transcription (e.g., lacUV5 promoter, tac promoter, lac promoter, lacUV5 promoter, lpp promoter, pLλ promoter, pRλ promoter, rac5 promoter, amp promoter, recA promoter, SP6 promoter, trp promoter, and T7 promoter), a ribosome binding site for initiating translation, and transcription/translation termination sequences. In cases where *E. coli* (e.g., HB101, BL21, DH5α etc.) is used as a host cell, the promoter and operator regions for the tryptophan biosynthesis pathway (Yanofsky, C., *J. Bacteriol.*, 158:1018-1024(1984)) and the leftward promoter from phage λ (pLλ promoter, Herskowitz, I. and Hagen, D., *Ann. Rev. Genet.*, 14:399-445(1980)) may be used as a regulatory region.

The vector injected into the host cell may be expressed in the host cell, and in this case, a large amount of acetoin reductase is obtained. In cases where the expression vector includes, for example, the lac promoter, the host cells may be treated with isopropylthio-β-D-galactoside (IPTG) to induce genetic expression.

Meanwhile, the vector that can be used in the present invention may be constructed by manipulating a plasmid (e.g., pKJ900 (derived from pBR322), pUC18, pTrc99A, pSTV28, pSC101, pGV1106, pACYC177, ColE1, pKT230, pME290, pBR322, pUC8/9, pUC6, pBD9, pHC79, pIJ61, pLAFR1, pHV14, pET22b, pGEX series, pET series, pUCP19, etc.), a phage (e.g., λ-Charon, M13, etc.) or a virus (e.g., SV40, etc.), which is often used in the art, but preferably, pKJ900 (Jung, Jae-Young, et al., Spectroscopic and photochemical analysis of proteorhodopsin variants from the surface of the Arctic Ocean *FEBS Letters* (2008) 582:1679-1684) is used.

The expression vector of the present invention includes a promoter sequence and a nucleotide sequence of a gene to be expressed (structural gene), and the sequences are preferably linked in the order of 5'-3'.

Meanwhile, the vector of the present invention includes, as a selective marker, an antibiotic agent-resistant gene that is ordinarily used in the art, and may include resistant genes against ampicillin, gentamycin, carbenicillin, chloramphenicol, streptomycin, kanamycin, geneticin, neomycin, and tetracycline.

According to a preferable embodiment of the present invention, the selection marker used in the present invention is ampicillin and/or chloramphenicol.

In the vector of the present invention, only the ribosomal binding site (RBS) and a nucleotide sequence including a portion necessary for enzyme expression are selected as a sequence such that the gene encoding the microbial-derived rhodopsin protein has the minimum length, including the enzyme overexpression function, and thus the selected sequence is preferably inserted into a host cell in view of reducing a metabolic burden of the host cell. According to a preferable embodiment of the present invention, pKJ900 vector was used.

(ii): Preparing Transformant

The method of the present invention includes a step for introducing the recombinant vector into a host cell to prepare a transformant.

Host cells that can stably and continuously clone and express the vector of the present invention are known in the art, and thus any host cell may also be used, and for example, at least one host cell selected from the group consisting of intestinal microflora and strains, including *E. coli* UT5600, *E. coli* JM109, *E. coli* BL21(DE3), *E. coli* RR1, *E. coli* LE392, *E. coli* B, *E. coli* X 1776, *E. coli* W3110, strains of the genus *Bacillus* (such as, *Bacillus subtilis* and *Bacillus thuringiensis*), *Salmonella typhimurium*, *Serratia marcescens*, and various *Pseudomonas* Spp., but is not limited thereto.

Preferably, the host cell is *E. coli*, and more preferably *E. coli* strain UT5600.

The vector of the present invention may be delivered into a host cell by a CaCl2 method (Cohen, S. N. et al., *Proc. Natl. Acad. Sci. USA*, 9:2110-2114(1973)), a Hanahan method (Cohen, S. N. et al., *Proc. Natl. Acad. Sci. USA*, 9:2110-2114(1973); and Hanahan, D., *J. Mol. Biol.*, 166: 557-580(1983)), an electroporation method (Dower, W. J. et al., *Nucleic. Acids Res.*, 16:6127-6145(1988)), and the like.

(iii): Obtaining Rhodopsin Protein

The method of the present invention includes a step for culturing the transformant to express the microbial-derived rhodopsin protein, thereby obtaining a rhodopsin protein.

According to a preferable embodiment of the present invention, the seed culture was diluted to 1:100 in LB medium supplemented with an antibiotic agent, and cultured until the absorbance at 600 nm reach 0.4. IPTG is then added to induce protein expression, and all-trans retinal was added and cultured, thereby obtaining a rhodopsin protein from rhodopsin-expressing cells.

In the method for preparing a proton-transport vesicle of the present invention, although the time sequential order of step (a) of preparing a photosystem II protein and the step (b) preparing a rhodopsin protein is changed, the purposes and effects of the present invention are not changed, and thus, the change in the time sequential step of steps (a) and (b) is also included in the present invention.

(c) Preparing Vesicles

The method of the present invention includes a step for hydrating lipids to prepare vesicles.

According to a preferable embodiment of the present invention, the lipids are POPC (1-palmitoyl-2-oleoyl-sn-glycero-3-phosphocholine) and POPE (1-palmitoyl-2-oleoyl-sn-glycero-3-phosphoethanolamine), and more preferably, POPC and POPE are mixed with a molar ratio of 3-5:1.

According to another preferable embodiment of the present invention, the hydration is conducted by using a buffer containing Tris, NaCl, $MgCl_2$, and $CaCl_2$.

(d) Freezing and Thawing Vesicles

The method of the present invention includes a step for freezing and thawing the vesicles in step (c).

The freezing process is carried out to make the synthesized vesicles into unilamellar forms, and in the present invention, liquefied nitrogen is used.

The thawing process is carried out at 40-60° C., and the size of vesicles can be made uniform through the thawing process.

(e) Reacting Product in Step (d) with Surfactant

The method of the present invention includes a step for reacting the product in step (d) with a surfactant.

As the surfactant, various surfactants known in the art may be used, and preferably n-dodecyl-β-D-maltopyranoside (DM) is used.

(f) Reacting Product in Step (e) with Photosystem II Protein in Step (a) and Rhodopsin Protein in Step (b)

The method of the present invention includes a step for reacting the product in step (e) with the photosystem II protein in step (a) and the rhodopsin protein in step (b).

According to another preferable embodiment of the present invention, in step (f), the product in step (e) is mixed with the photosystem II protein in step (a) and the rhodopsin protein in step (b) at a molar ratio of 300-700:1, more preferably a molar ratio of 400-600:1, and still more preferably at a molar ratio of 450-550:1.

According to a still another preferable embodiment of the present invention, the photosystem II protein in step (a) and the rhodopsin protein in step (b) are mixed at a molar ratio of 1:1.

In this manner, proton-transport vesicles reconstituted with heterologous photosensitive proteins can be prepared.

Advantageous Effects

Features and advantages of the present invention are summarized as follows:

(a) The present invention provides proton-transport vesicles reconstituted with a microbial-derived rhodopsin and plant-derived photosystem II proteins and a method for preparing the same.

(b) The proton-transport vesicle of the present invention has an absorption wavelength band of the entire region of visible light since the heterologous photosensitive proteins are inserted and located in the bilayer of a single phospholipid bilayer liposome to utilize different light absorption bands of the respective proteins.

(c) Therefore, the limited efficiency caused by utilizing only a particular wavelength in conventional microorganisms or artificial vesicles was improved and the wavelength range to be used can be expanded to the entire wavelength region of visible light.

(d) Meanwhile, the fusion system of the rhodopsin protein and the photosystem II protein of the present invention is used to improve the conventional pumping ability efficiency of hydrogen ions inside or outside the phospholipid membrane of the protein, and thus, the present invention is expected to be applied to the extracellular production of ATP or to be industrially applicable in various fields, such as photo-catalysts and solar cells.

DETAILED DESCRIPTION

MODE FOR CARRYING OUT THE INVENTION

Hereinafter, the present invention will be described in detail with reference to examples. These examples are only for illustrating the present invention more specifically, and it will be apparent to those skilled in the art that the scope of the present invention is not limited by these examples.

EXAMPLES

Example 1: Extraction and Purification of Photosystem II Protein Complex

A plant protein complex was prepared using spinach or *Arabidopsis thaliana* as needed, and a method of purifying and isolating a protein complex is as follows:

First, in order to isolate a photosystem II protein complex, buffer solutions were prepared as shown in table 1.

TABLE 1

| | |
|---|---|
| Buffer A | 0.5% milk powder or sorbitol, 0.4M NaCl, 0.2% $MgCl_2$, 20 mM Tricine/KOH pH 7.8, 0.2 mM PMSF, 0.2 mM Benzamidine, 1 mM ε-aminocaproic acid |
| Buffer B | 0.15 NaCl, 0.5% $MgCl_2$, 20 mM Tricine/KOH pH 7.8, 0.2 mM PMSF, 0.2 mM Benzamidine, 1 mM ε-aminocaproic acid |
| Buffer C | 15 mM NaCl, 0.5% $MgCl_2$, 20 mM Hepes KOH pH 7.5 |
| Buffer D | 0.4M sorbitol, 15 mM NaCl, 5 mg $MgCl_2$, 10 mM Hepes KOH pH 7.5 |
| Surfactant | 0.25-4% α-DM (usually: 3%), 15 mM NaCl, 5 mg $MgCl_2$ |

For the isolation and purification of plant protein complex, the separation of thylakoid membranes in a plant was first conducted, and the whole process was carried out at 4° C./dark room. Specifically, plant leaves were cut at intervals of 1 cm using a shaving knife, and then reacted with a buffer A solution prepared in advance. After 15 minutes, the reaction solution was filtered through a 0.5-1 mm pore size filter, and the filtered solution was centrifuged at 4° C./1000 g for 5 minutes. After the supernatant was removed, the remaining material was reacted with buffer A, followed by shaking using a vortex mixer. Thereafter, centrifugation was conducted at 4° C./1000 g for 5 minutes. After the supernatant was removed, the remaining material was reacted with buffer B, followed by mixing using a vortex mixer. Thereafter, the mixture was conducted at 4° C./1000 g. Thereafter, the supernatant was removed, and then, the remaining material was reacted with buffer C, followed by mixing using a vortex mixer. Thereafter, the mixture was conducted at 4° C./1000 g, and placed in liquefied nitrogen to lower the temperature, and stored at −80° C. before use.

Figure 1:
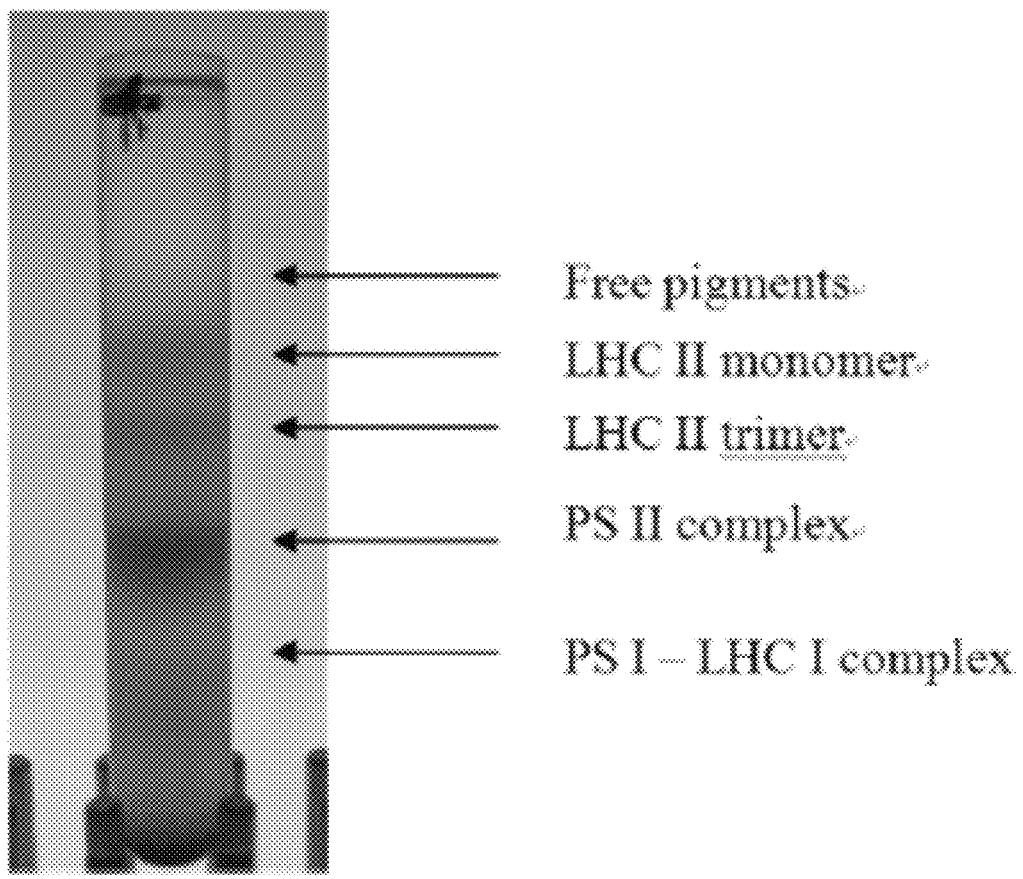
FIG. 1 is an image showing the results of isolating a plant-derived photosystem II protein by a sucrose gradient method.
Figure 2:
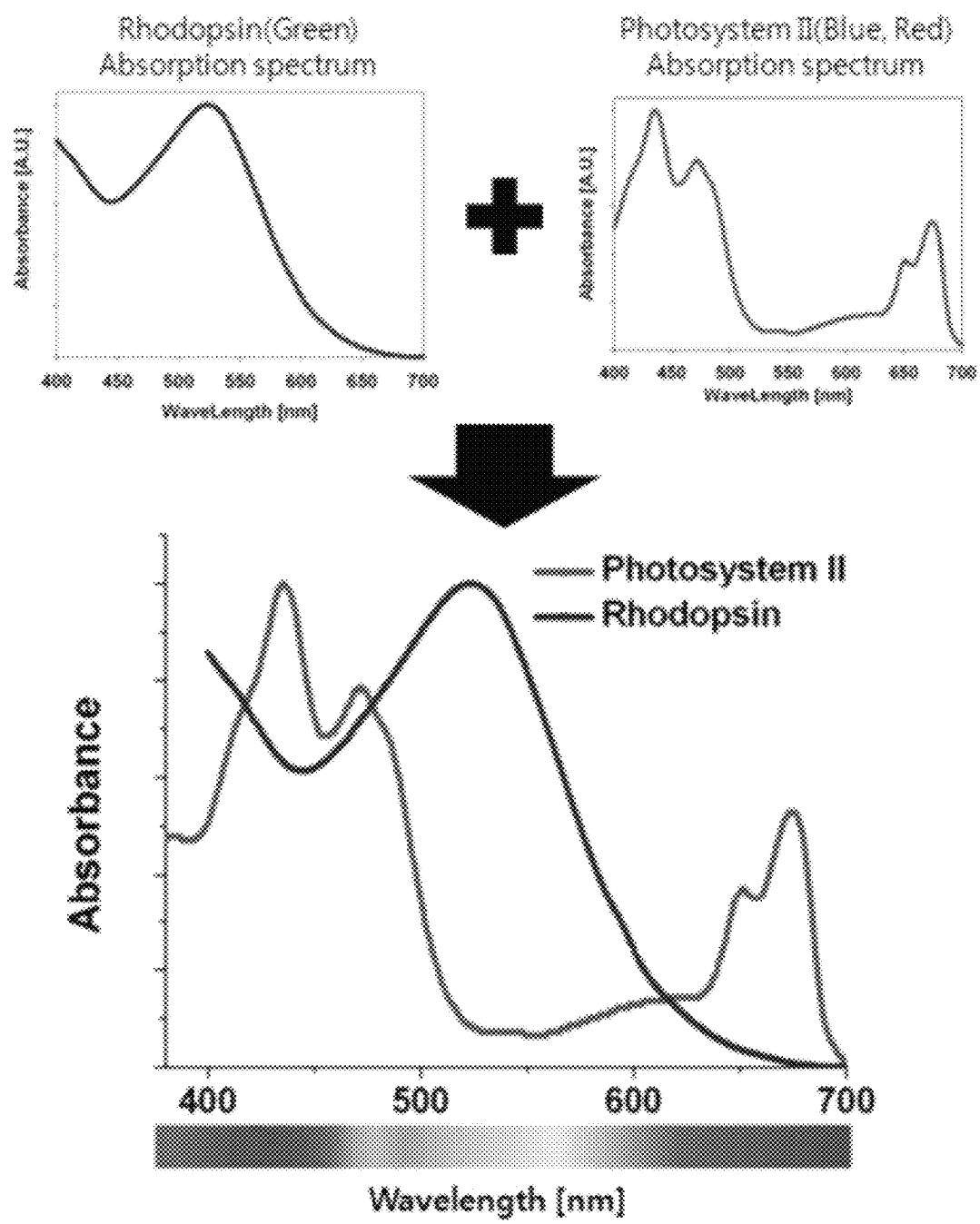
FIG. 2 illustrates visible light absorbance of the photosystem II protein and the rhodopsin protein.
Figure 3:
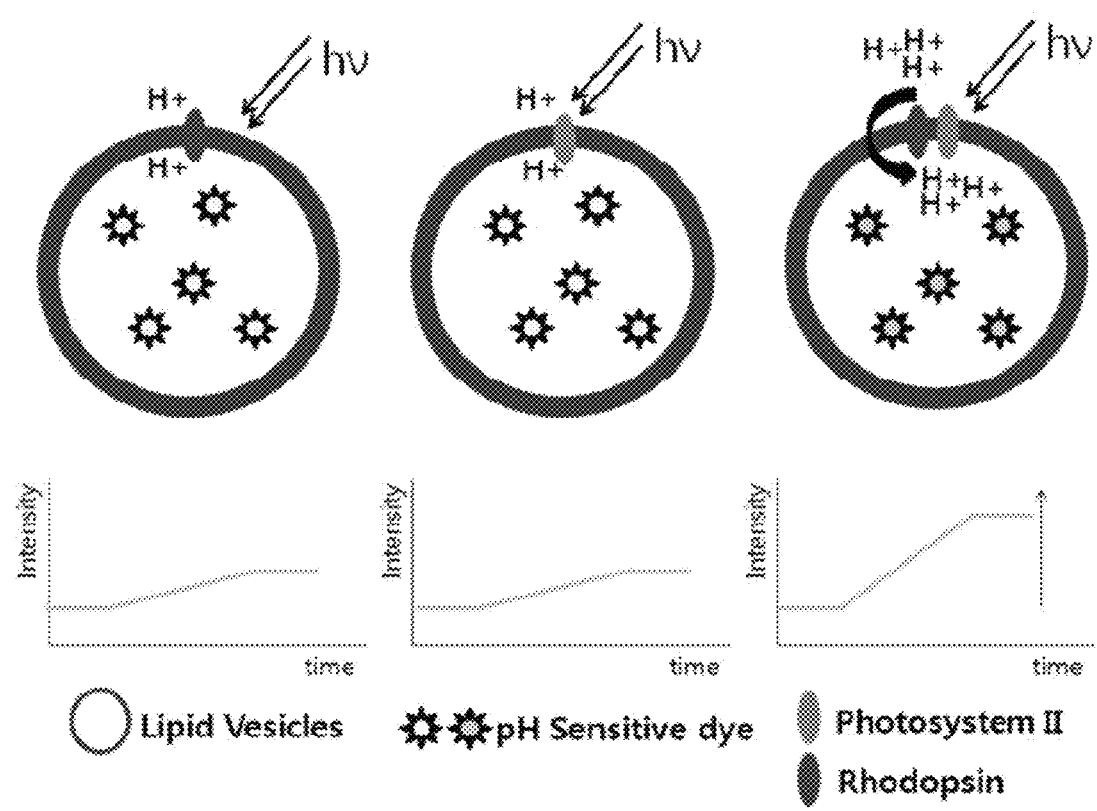
FIG. 3 illustrates relative hydrogen ion pumping abilities of the photosystem II protein, the rhodopsin protein, and the photosystem II protein and rhodopsin protein reconstituted into the cellular membrane.

For the isolation of the photosystem II protein complex, the thylakoid membranes extracted from plant leaves were used, and a sucrose gradient method was employed. Specifically, the temperature of the thylakoid membranes was adjusted to 4° C. from −80° C., and then a gradient solution (0.5 M sucrose, 20 mM Hepes pH 7.8, and surfactant DM 0.03%) was prepared while the temperature thereof was maintained at 4° C. Thereafter, the thylakoid lipid membranes were reacted with the gradient solution. Thereafter, centrifugation was conducted at 4° C./18,000 g, and then the supernatant was removed. Thereafter, the remaining material was reacted with 10 mM Hepes pH 7.8 and 5 mM EDTA, followed by centrifugation at 4° C./18,000 g. After the reaction with 10 mM Hepes pH 7.7 and 0.6% DM and the reaction using a vortex mixer, the resulting product was transferred into a gradient tube while the supernatant was maintained. Thereafter, the plant protein complex was isolated and purified through sucrose density. The sucrose solution entering in each layer was separated into five stages from 0.1 M to 1 M sucrose in the base of 20 mM Hepes pH 7.8, 0.03% (FIG. 1). Then, centrifugation was conducted at 4° C./120,000 g for 24 hours. The concentration of the extracted protein was determined by the concentration of chlorophyll contained in the protein after the reaction with 80% acetone. The concentration was obtained by equation 1 below:

$$[Chl]=[(20.2*A_{645}+9.02*A_{663})*V_a]/V_s \quad \text{[Equation 1]}$$

wherein $A_{645}$ and $A_{663}$ are absorbance values at 645 nm and 663 nm in the absorption spectrum; $V_a$ is the amount of 80% acetone added; and $V_s$ is the amount of the sample.

Example 2: Expression and Purification of Rhodopsin (1) Preparation of E. coli Transformant The plasmid pKJ900-PR, which is a vector containing the gene (SEQ ID NO: 1) encoding the proteorhodopsin protein, was introduced into E. coli strain UT5600 (NEB, UK). The UT5600 strain has a deficiency in a kind of membrane protein protease, and is useful for the stable expression of membrane proteins. First, the capacity of E. coli strain UT5600 was improved by a method using a $CaCl_2$ reagent. The E. coli strain UT5600 was mixed with an expression vector, and transformed by a thermal shock. Ampicillin (USB), which is an antibiotic agent suitable for the antibiotic agent-resistant gene contained in the expression vector, was plated on LB medium at a final concentration of 50 μg/ml to form colonies.

(2) Expression of Proteorhodopsin and Preparation Membrane Vesicles in Cells

For absorption spectroscopy and proton pumping measurements, proteorhodopsin was expressed using the plasmid pKJ900-PR in E. coli strain UT5600. The selected transformants were cultured overnight, diluted to 1:100 in 500 ml of LB supplemented with ampicillin (50 μg/ml) and chloramphenicol (34 μg/ml) in a 1 L flask, and then cultured in a 35° C. incubator until the absorbance at 600 nm reached 0.4 absorbance unit (AU). In order to obtain a protein for hydrogen ion transport measurement, IPTG was added at a final concentration of 0.8 mM to induce protein expression, and here, the all-trans retinal was added at a final concentration of 5 uM. After 4 hours, the cells were harvested by centrifugation, and resuspended in 50 mM Tris-HCl (pH 7.0) containing 150 mM NaCl. Rhodopsin-expressed E. coli cells were lysed by sonication at 4° C., and the cell debris was removed by a low-speed centrifuge (3,600×g, 15 min). Finally, the membranes were precipitated at 95,000×g for 1 hour at 4° C., and resuspended using 50 mM Tris (pH 7.0) containing 150 mM NaCl at 4° C. The culture was gently vibrated in an extraction buffer (1% sodium dodecyl maltoside (DM), 150 mM NaCl, 50 mM Tris-buffer (pH 7.0)) at 4° C. for 4-6 hours, to extract rhodopsin from the membranes. The extracted protein was obtained by taking the supernatant after the centrifugation at 30,000×g. Membranes without receptor proteins were prepared by the same procedure, and then used as a control.

(3) Purification and Isolation of his-Tagged Proteorhodopsin

Proteins containing the 6-histidine residue at the C-terminus were isolated using $Ni^{2+}$-NTA agarose beads (Qiagen, Valencia, Calif., U.S.A.). E. coli membranes containing proteorhodopsin were lysed in 1% DM containing 150 mM NaCl, 10 mM imidazole, and 50 mM Tris (pH 7.0), and then incubated together with beads for 16 hours at 4° C. Protein-conjugated beads were washed with 50 mM imidazole, and eluted with 250 mM imidazole, 0.02% DM, and 50 mM Tris-buffer. The obtained proteins dissolved in 0.02% DM were used to measure the maximum absorption wavelength.

Figure 4:
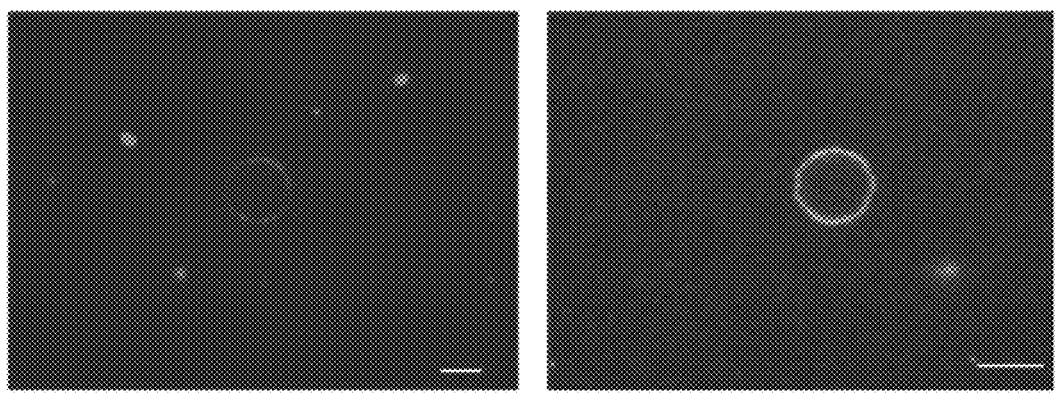
FIG. 4 shows fluorescent microscopic images obtained after the photosystem II protein and the rhodopsin protein are reconstituted, respectively.

Example 3: Cellular Membrane Reconstitution of Photosystem II (PS II) Protein Complex For the preparation of proteoliposomes for realizing artificial evolution through membrane reconstitution, sub-micron sized membranes need to be synthesized. Specifically, POPC (1-palmitoyl-2-oleoyl-sn-glycero-3-phosphocholine) and POPE (1-palmitoyl-2-oleoyl-sn-glycero-3-phosphoethanolamine) phospholipids were dissolved in chloroform at a molar ratio of 80:20 while the total amount of lipids was set to be 5 mg. Thereafter, the mixture was placed in a round flask, and then chloroform (organic solvent) was removed using argon or nitrogen gas. Thereafter, the resulting product was stored in a vacuum state for about 3 hours to further remove all the remaining organic solvent. Then, 10 mM HEPES pH 7.4 solution was placed in a 1 mL flask, followed by reaction, and then, the reaction product was reacted at room temperature using a vortex mixer for 1 hour. Then, the reaction product was put into liquid nitrogen to be completely frozen, thereby causing a change in the lipid phase, and then placed in water to return to room temperature. The reaction solution was subjected to the following work five times, and then passed through a 100 nm polycarbonate filter to synthesize 100 nm cell membranes. Then, a surfactant solution was added such that the ratio of the surfactant, DM, and lipid was 2% (w/w). After reaction for 1 hour, the PS II protein was inserted. Here, the concentration of the protein calculated for protein extraction was used, and the ratio of protein and lipid was set to 1:500. Then, the surfactant was removed through dialysis and SM2 bio-beads to allow the protein to be inserted between the cell membranes, thereby completing proteoliposomes. Then, for easy observation under a microscope, the completed proteoliposomes were dropped on an ITO glass, and then placed in a vacuum for about 12 hours. Then, after the reaction with 15 mM Hepes pH 7.4 and 10 mM $MgCl_2$ solution, 1.5 V, 10 Hz alternating current electricity was applied to both electrodes for about 4 hours, thereby completing 10-100 micron proteoliposomes. For the observation using a fluorescence microscope, the fluorescence of chlorophyll, which is a self-fluorescence of the PSII, was used. For the excitation wavelength, 488-nm laser was used, and the sample was identified using a 650-700 nm fluorescent band-pass filter. The left panel of FIG. 4 is a fluorescence microscopic image of the proteoliposome synthesized by the following method.

Example 4: Preparation of Phospholipid-Based Proteoliposomes Containing Membrane Protein Proteorhodopsin In order to reconstitute the membrane protein, proteorhodopsin (PR), into the artificially synthesized vesicle membrane, vesicles not containing membrane proteins were first prepared. Vesicles may be artificially synthesized from various lipids, but the vesicles of the present invention were synthesized from a lipid mixture in which POPC (1-palmitoyl-2-oleoyl-sn-glycero-3-phosphocholine) and POPE (1-palmitoyl-2-oleoyl-sn-glycero-3-phosphoethanolamine) were mixed at a particular ratio. The lipid mixture was dried to make a lipid film, which was then gently hydrated using a buffer (pH 7.01) containing 20 mM Tris and 150 mM NaCl. In order to make the synthesized vesicles into a unilamellar form before the reconstitution with the membrane proteins, the vesicles were subjected to freezing using liquefied nitrogen and thawing at 51° C., and then vesicles with a predetermined size were separated. The extrusion through a polycarbonate filter was carried out to obtain vesicles with a predetermined size. The thus synthesized single-lamella vesicles with a predetermined size containing no membrane proteins were reacted with DM (n-dodecyl-β-D-maltopyranoside) for a predetermined period of time, and then reacted with proteorhodopsin.

Figure 5:
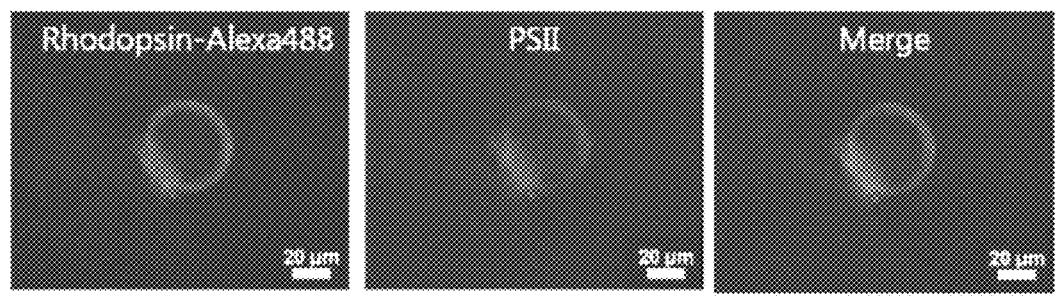
FIG. 5 shows fluorescent microscopic images obtained by photographing photosystem II (center panel), rhodopsin protein (left panel), and photosystem II and rhodopsin proteins (right panel), which were reconstituted into one phospholipid.

The purified proteorhodopsin dissolved in a buffer (pH 7.01) containing 20 mM Tris, 150 mM NaCl and 0.02% DM was reacted, at 4° C., with the vesicles synthesized in the above procedure, and then, in order to remove DM contained in the buffer, the reaction product was dialyzed using a dialysis tubing with a 50 kDa MWCO in buffer (20 mM Tris, 150 mM NaCl, pH 7.01) at 4° C. for 4 days or more. Then, after the reaction with 15 mM Hepes pH 7.4 and 10 mM $MgCl_2$ solution, 1.5 V, 10 Hz alternating current electricity was applied to both electrodes for about 4 hours, thereby completing 10-100 micron proteoliposomes. In order to examine the sample using a fluorescence microscope, a fluorescent dye, Alexa488, was used for proteorhodopsin. The carboxyl group of Alexa488 fluorescent molecules was reacted with the lysine residue of proteorhodopsin to generate green fluorescence. For the excitation wavelength, a 488-nm laser was used, and the sample was identified using a 520- to 550-nm fluorescent band-pass filter. The leftmost panel of FIG. 5 shows a proteoliposome synthesized by the following method.

Figure 6:
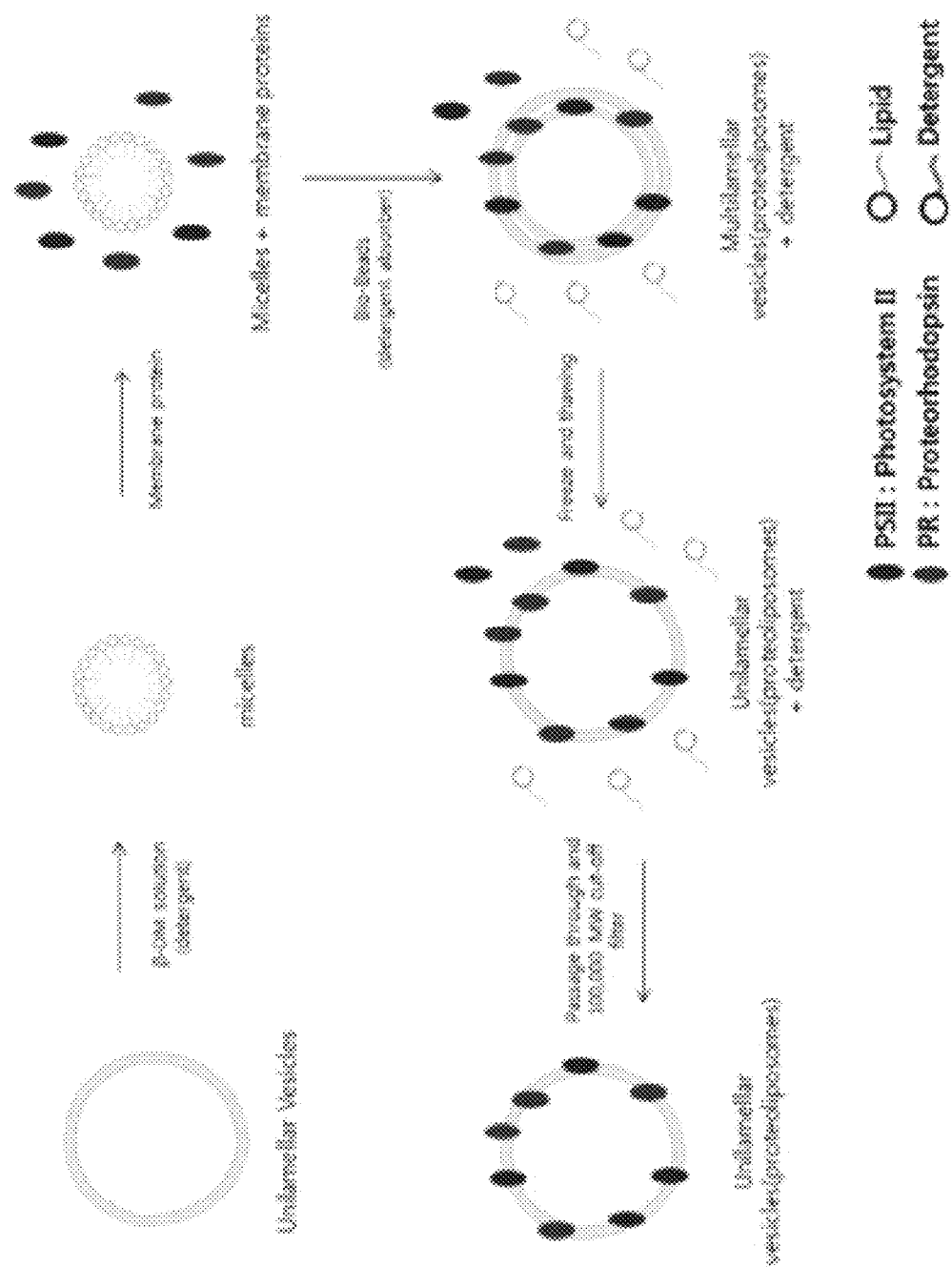
FIG. 6 illustrates a procedure of reconstituting photosystem II and rhodopsin proteins into one phospholipid.

Example 5: Synthesis of Liposomes Containing Heterologous Membrane Proteins, Photosynthesis II (PS II) and Proteorhodopsin In order to reconstitute the membrane proteins, extracted from fungi and plants, into a single cell membrane, the reaction was carried out under optimal conditions for both the proteins. The POPC and POPE lipid mixtures with a concentration used in the above reconstitution process were prepared, sufficiently dried, and hydrated with a buffer (pH 7.8) containing 15 mM Tris, 10 mM NaCl, 10 mM $MgCl_2$, and 10 mM $CaCl_2$. The synthesized vesicles were subjected to the freezing-thawing process described above, separated into a predetermined size, reacted with a surfactant, and finally reacted with heterologous proteins and the lipid at a ratio of 1:500. In order to remove unreacted membrane proteins and surfactant after the sufficient reaction, the reaction product was dialyzed in a buffer (pH 7.8) containing 15 mM Tris, 10 mM NaCl, 10 mM 10 mM $MgCl_2$, and 10 mM $CaCl_2$. FIG. 6 is a schematic diagram of a method for synthesizing heterologous membrane proteins into one cell membrane.

Figure 7:
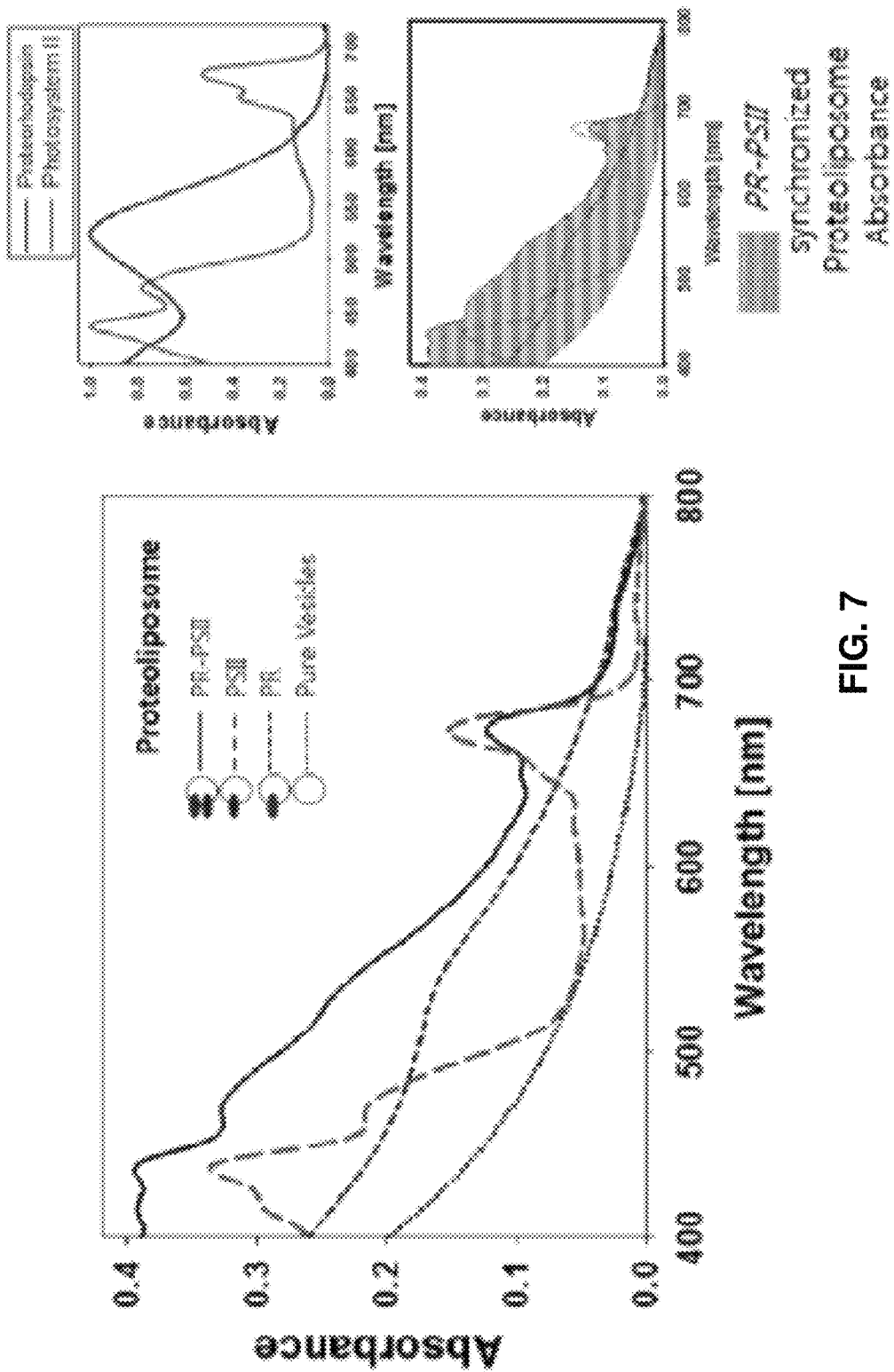
FIG. 7 is a graph showing the increase and expansion of the light absorption in the region of visible light due to the reconstitution of photosystem II and rhodopsin proteins into one phospholipid.

Absorption spectra and fluorescence microscopy were used to confirm whether the synthesized heterologous proteins were inserted into the cell membrane. A 100,000 MW filter and a centrifuge were used to remove the unreacted PSII and proteorhodopsin. Considering that the heterologous proteins are smaller than 100,000 MW and thus pass through the filter, the fact that proteins not inserted into the cell membrane pass through the filter was employed. Thereafter, the absorbance of the synthesized sample was measured to examine whether the heterologous proteins are all contained (FIG. 7).

The proteoliposomes made to examine the reconstitution state of the heterologous membrane proteins were dropped into an ITO glass, made into a lipid film form, and then swollen using a buffer containing 2 mM HEPES and 10 mM NaCl in the conditions of alternating current electricity of 1.5 V, 10 Hz, and then, giant unilamellar vesicle (GUV)-form proteoliposomes with a size of several tens of microns were observed using a microscope. For the observation using a fluorescence microscope, a fluorescent dye, Alexa488, was used for proteorhodopsin. The carboxyl group of Alexa488 fluorescent molecules was reacted with the lysine residue of proteorhodopsin to generate green fluorescence. For PSII, a red fluorescent pigment of chlorophyll contained in PSII itself was used.

Therefore, proteorhodopsin and PSII could be confirmed by green fluorescence and red fluorescence, respectively, which have different wavelengths of fluorescence. In addition, the fluorescence generated by exciting fluorescent molecules using Alexa488 and chlorophyll absorption wavelength 450-480 nm were observed at 520-550 nm (green, Alexa488) and 640-700 nm (red, chlorophyll), respectively, using a bandpass filter.

FIG. 5 shows fluorescence microscopic images of the same sample, and green (left panel) represents the fluorescence of proteorhodopsin; red (center panel) represents the fluorescence of PSII; and orange (right panel) is shown in a merge image of the two images.

Although the present invention has been described in detail with reference to the specific features, it will be apparent to those skilled in the art that this description is only for a preferred embodiment and does not limit the scope

What is claimed is:

1. Proton-transport vesicles, each comprising:
   (a) a single phospholipid bilayer liposome;
   (b) a proteorhodopsin; and
   (c) a photosystem II protein,
   wherein the proteorhodopsin and the photosystem II protein are inserted in the bilayer of the liposome.

2. The proton-transport vesicles of claim 1, wherein the photosynthesis II protein is a plant-derived protein.

3. The proton-transport vesicles of claim 1, wherein the proteorhodopsin absorbs 500- to 600-nm light, corresponding to green wavelength in the wavelength range of visible light, to generate protons.

4. The proton-transport vesicles of claim 1, wherein the photosystem II protein absorbs 400- to 500-nm light and 600- to 700-nm light, respectively corresponding to blue wavelength and red wavelength in the wavelength range of visible light, to generate protons.

5. The proton-transport vesicles of claim 1, wherein the plant is selected from the group consisting of spinach, *Arabidopsis thaliana*, rice, and corn.

6. A method for preparing proton-transport vesicles, the method comprising the steps of:
   (a) preparing a photosystem II protein;
   (b) preparing a proteorhodopsin;
   (c) hydrating lipids to prepare vesicles;
   (d) freezing and thawing the vesicles in step (c);
   (e) reacting the product in step (d) with a surfactant; and
   (f) reacting the product in step (e) with the photosystem II protein in step (a) and the proteorhodopsin in step (b).

7. The method of claim 6, wherein the preparing of the proteorhodopsin in step (b) comprises the following steps of:
   (i) inserting a nucleotide sequence encoding a microbial-derived proteorhodopsin into an expression vector to construct a recombinant vector;
   (ii) introducing the recombinant vector into a host cell to prepare a transformant; and
   (iii) culturing the transformant to express the microbial-derived proteorhodopsin, thereby obtaining a proteorhodopsin.

8. The method of claim 7, wherein the host cell is *E. coli*.

9. The method of claim 6, wherein in step (f), the product in step (e) is mixed with the photosystem II protein in step (a) and the proteorhodopsin in step (b) at a molar ratio of 300-700:1.

\* \* \* \* \*